United States Patent [19]

Powers et al.

[11] Patent Number: 5,342,403

[45] Date of Patent: Aug. 30, 1994

[54] INTEGRATED DEFIBRILLATOR/MONITOR ARCHITECTURE WITH DEFIBRILLATOR-ONLY FAIL-SAFE MODE OF OPERATION

[75] Inventors: Daniel J. Powers, McMinnville; Judith Cyrus, Newberg, both of Oreg.; Steve Kootstra, Roseville, Calif.; Art Burkhalter, Monmouth, Oreg.; J. Daren Bledsoe, McMinnville, Oreg.; David C. Shultheis, McMinnville, Oreg.; Dan Jordan, McMinnville, Oreg.

[73] Assignee: Hewlett-Packard Corporation, Palo Alto, Calif.

[21] Appl. No.: 46,280

[22] Filed: Apr. 9, 1993

[51] Int. Cl.$^5$ ............................................. A61N 1/39
[52] U.S. Cl. ........................................................ 607/5
[58] Field of Search ............................................. 607/5–8

[56] References Cited

U.S. PATENT DOCUMENTS

| | | |
|---|---|---|
| 3,614,955 | 10/1971 | Mirowski ............................. 607/6 |
| 3,805,795 | 4/1974 | Denniston et al. .................... 607/6 |
| 4,432,375 | 2/1984 | Angel et al. .......................... 607/6 |
| 4,614,192 | 9/1986 | Imran et al. .......................... 607/5 |
| 4,619,265 | 10/1986 | Morgan et al. ....................... 607/6 |
| 4,974,600 | 12/1990 | Reyes .................................. 607/5 |

FOREIGN PATENT DOCUMENTS

| | | | |
|---|---|---|---|
| 0038080 | 10/1981 | European Pat. Off. ................ 607/6 |
| 0299338 | 1/1989 | European Pat. Off. ................ 607/5 |
| 0353341 | 2/1990 | European Pat. Off. ................ 607/5 |
| 1272570 | 8/1961 | France ................................... 607/5 |

Primary Examiner—William E. Kamm

[57] ABSTRACT

A defibrillator/monitor architecture is disclosed with a defibrillator-only mode of operation to provide for shocking a patient notwithstanding failure of the monitor subsystem. The defibrillator/monitor subsystem is partitioned into a defibrillator subsystem and a monitor subsystem. The defibrillator subsystem includes the patient charging circuits and other components necessary to carry out basic defibrillation. The monitor subsystem includes an ECG front-end, CRT display, data recorder and other features. In normal operation, the defibrillator subsystem relies on periodic ECG data ready interrupts from the monitor subsystem for system timing. In the event that the ECG interrupts do not arrive within a predetermined time limit, the monitor subsystem is presumed dead and the defibrillator subsystem switches to defibrillator-only mode of operation, in which system timing is provided by a local standby timer.

20 Claims, 4 Drawing Sheets

INTEGRATED DEFIBRILLATOR/MONITOR ARCHITECTURE WITH DEFIBRILLATOR-ONLY FAIL-SAFE MODE OF OPERATION

BACKGROUND OF THE INVENTION

A defibrillator delivers measured amounts of electrical energy ("shocks") to a patient in a procedure called defibrillation. The energy is administered to the patient through paddles or pads which are connected to the defibrillator unit through a cable, and arranged in electrical contact with the patient's chest. Generally, a shock is delivered to the patient when a user presses two discharge buttons concurrently. The discharge buttons may be located on external paddle assemblies and/or on the defibrillator unit itself.

Defibrillator systems generally also include an integral monitor for acquiring electrocardiographic (ECG) data from the patient. The ECG data may be displayed on a display device in the defibrillator unit such as a CRT, printed by a recorder (which also may be provided in the defibrillator system), and/or used to control synchronized cardioversion. Synchronized cardioversion is a procedure in which the defibrillator shocks are synchronized with the ECG's R-wave. It is essential for synchronized cardioversion, therefore, that the monitor be operational and coupled to the defibrillator or an external ECG source provided to the defibrillator.

Various equipment failures can occur in a defibrillator system other than failures in the defibrillator per se, i.e. the patient shock delivery circuits. For example, the ECG front-end may fail so it cannot acquire ECG data. Or, signal processing hardware and/or software may fail so that even though ECG raw data is acquired, the R-wave cannot be identified in that data. Other failures may disable the CRT display capability, or perhaps affect the recorder unit. In known defibrillator systems, virtually any significant failures are detected and render the unit unusable. To provide maximum reliability in this life critical application, however, the basic defibrillator shock-delivery function should be made available if possible, not withstanding one or more of a myriad of possible failures in the defibrillator system. The need remains, therefore, for a defibrillator/monitor design that would allow defibrillation of a patient in an emergency situation even though one or more failures have occurred in the system.

DETAILED DESCRIPTION OF THE PREFERRED EMBODIMENT

Figure 1:
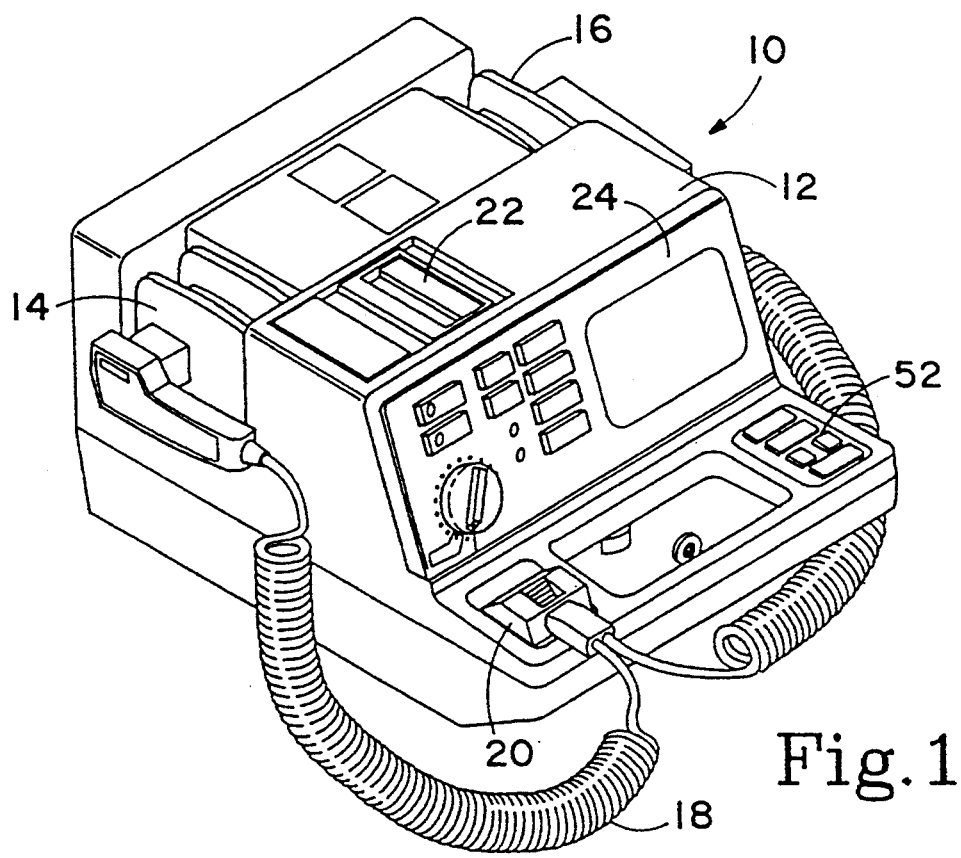
FIG. 1 is a perspective view of an integrated defibrillator/monitor system.

A defibrillator/monitor system 10 is shown in FIG. 1. The defibrillator/monitor incorporates a modular design which is arranged to decouple the monitor and defibrillator subsystem control functions so that a monitor subsystem failure will not prevent the defibrillator subsystem from functioning. In general, the defibrillator/monitor base unit 10 is built in a sturdy case 12 and may include a battery system for portable use. An external paddle assembly, for example external paddles 14, 16, is connected to the base unit through a plug assembly 20. The plug assembly 20 includes cables, for example cable 18. The base unit may include a built-in recorder 22 for providing hard copy records of defibrillator activity. The base unit further includes a front panel 24 which includes keyswitches for user input as will be further described below.

Figure 2:
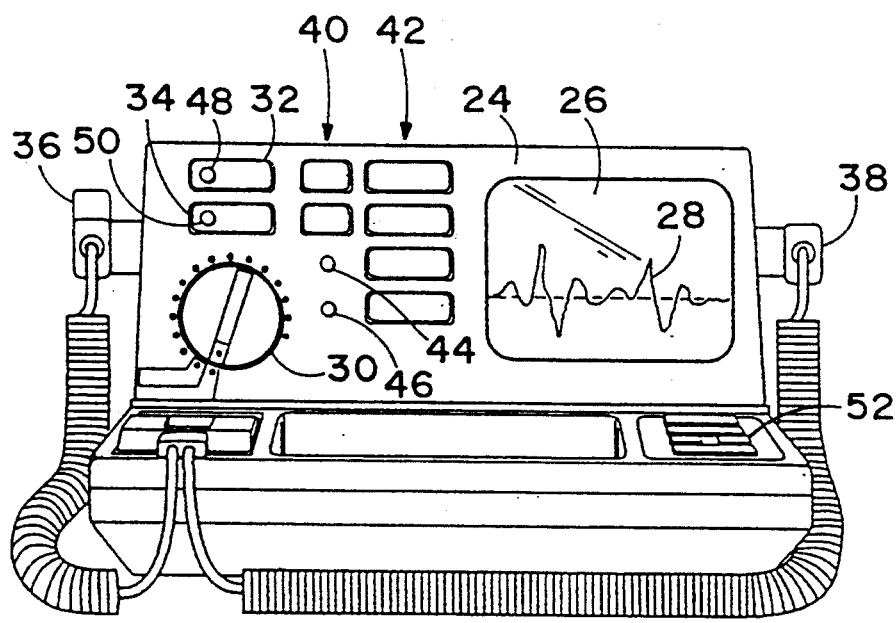
FIG. 2 is a front view of the defibrillator/monitor system of FIG. 1.

FIG. 2 shows the defibrillator/monitor system of FIG. 1 in front view. As illustrated, the front panel 24 includes a CRT display 26, which may be used to display an ECG waveform 28 as well as other information such as configuration settings or energy level. The front panel also includes an energy selection knob 30 for setting a defibrillation energy level. The system optionally may include a pacer apparatus 52 although such is not pertinent to the present invention. A series of buttons 42 are used for controlling monitoring functions. Another series of buttons 40 are used for operating the recorder 22.

User controls for defibrillation include the following: first, a charge button 32 is used to begin charging a patient circuit. The patient circuit (not shown) includes means for storing electrical energy, such as a capacitor, for subsequently delivering that energy to the patient by discharging the capacitor through the plug assembly 20 and the paddles 14, 16. The patient circuit also includes means for charging the capacitor to the energy level indicated by the energy selection knob 30. A charge-done light 48 is provided on the charge button 32 for indicating when the capacitor is charged to the selected energy level. Another push-button 34 is used for selecting a synchronized mode of operation for synchronized cardioversion. An indicator light 50 is provided on push-button 34 for indicating when the synchronized mode is in effect. The front panel 24 also includes an AC power light 44 for indicating that AC power is connected to the unit and a battery-charged light 46 for indicating that the battery is charging.

In normal defibrillator operation, a user selects a desired energy level using the energy selection knob 30 and then actuates the charge button 32 to begin charging the unit to the selected energy level. After the unit is so charged, as indicated by illumination of the charge-done light 48, the user may shock the patient at will by pressing discharge buttons 36, 38, which are located on the paddle assemblies 14, 16 respectively. At the time of discharge, the paddles are in contact with the patient's chest, rather than stored in the base unit as illustrated. While the patient's circuit capacitor is charging, the energy level is displayed (and periodically updated) on the CRT display 26. Other data may be displayed on the display 26 as well such as an indication of the quality of the patient contact. The monitor may be set for acquiring ECG data. Following discharge, an event summary may be printed by the recorder 22.

Treatment for certain arrhythmias require synchronizing a defibrillator shock with the ECG's R-wave. It is essential that this R-wave is detected to avoid inducing ventricular fibrillation. To start cardioversion, the energy selection knob 30 is turned to a "monitor on" position. The ECG leads in use are identified by a lead select procedure and the synchronized button 34 is actuated to place the instrument in sync mode. The message SYNC appears on the CRT display 26.

Figure 3:
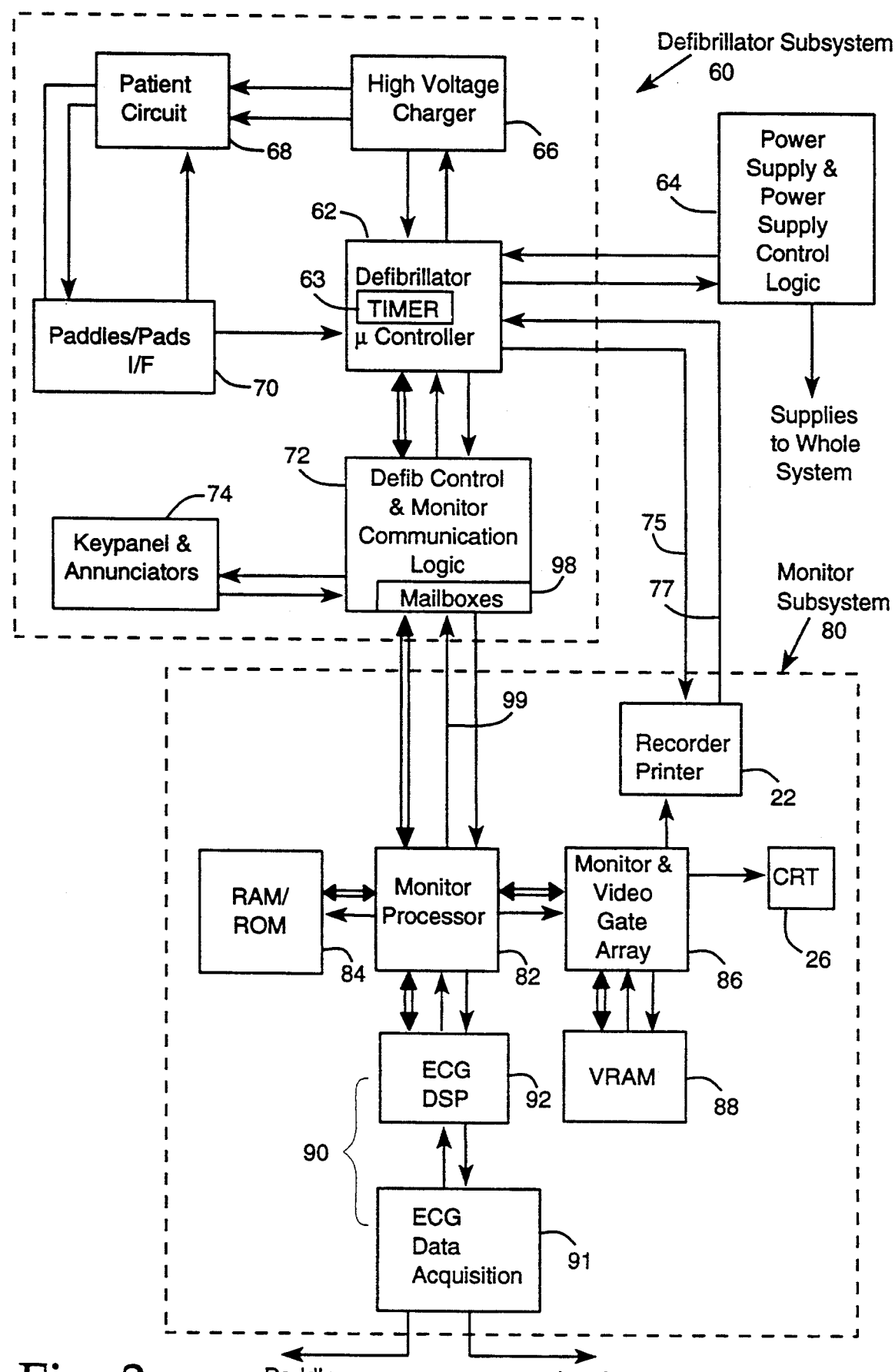
FIG. 3 is a functional block diagram of defibrillator and monitor subsystems in the defibrillator/monitor system of FIG. 1.

FIG. 3 is a functional block diagram of the defibrillator/monitor system described above. FIG. 3 shows a defibrillator subsystem 60 and a monitor subsystem 80. These two subsystems incorporate most of the defibrillator/monitor system apparatus, with notable exception of the power supply and power supply control logic 64. The defibrillator subsystem 60 is controlled by a defibrillator microcontroller 62. The microcontroller may be implemented, for example, by an 80C196 processor or the like, such devices being known and commercially available. The defibrillator controller 62 includes an internal timer 63, further described below. Essentially, all of the defibrillator operations described herein are controlled by the controller 62. A high voltage charger circuit 66 is coupled to the controller 62 and also coupled to a patient's circuit 68. As noted, the patient circuit includes a capacitor for storing energy for defibrillating a patient. Patient circuit 68 is coupled to a pads/paddles interface circuit 70 which is arranged for connection to the plug assembly 20 of FIG. 1. High voltage charger 66 and the pads/paddles interface 70 are controlled by the controller 62 and they in turn provide feedback to the controller such as a charge-done indication or a discharge message responsive to user actuation of the discharge buttons described above.

Defibrillator controller 62 also is coupled to defibrillator communication logic 70 by means of both data and control pads as indicated in the drawing. The defibrillator communication logic may be implemented as a gate array with suitable software stored therein whereby such other combinations of hardware and/or software as a designer may choose. The defib communication logic further includes mailboxes 98 which are described in greater detail below.

Finally, defib communication logic 72 is coupled to keypanel and annunciators circuitry 74. Keypanel and annunciators circuitry communicates with the front panel 24 for reading the states of the various keypanel buttons and controls discussed above, and for controllably actuating the various indicator lights also discussed above. Circuitry 74 also includes audible tone generator for indicating a charge-done to a user.

The monitor subsystem 80 is controlled by monitor processor 82 which may be, for example, an 80960KA type processor. Random access memory (RAM) and read-only memory (ROM) 84 are coupled to the processor 82 to provide general working memory, program and data storage, including power-up configuration data. An ECG front-end comprises ECG data acquisition means 91 and ECG digital signal processing (DSP) circuitry 92. The data acquisition means 91 is coupled to the defibrillator paddles or patient leads for acquiring ECG data. The raw data is processed in the ECG DSP 92 and the processed data provided to the monitor processor 82. Monitor processor 82 further provides ECG data to the defibrillator subsystem as further described below.

Monitor and video gate array 86 generates data for driving the CRT display 26 and for recording by the recorder 22. A video RAM (VRAM) storage 88 is coupled to the video data array 86 for providing appropriate video data to the CRT 26.

Figure 4:
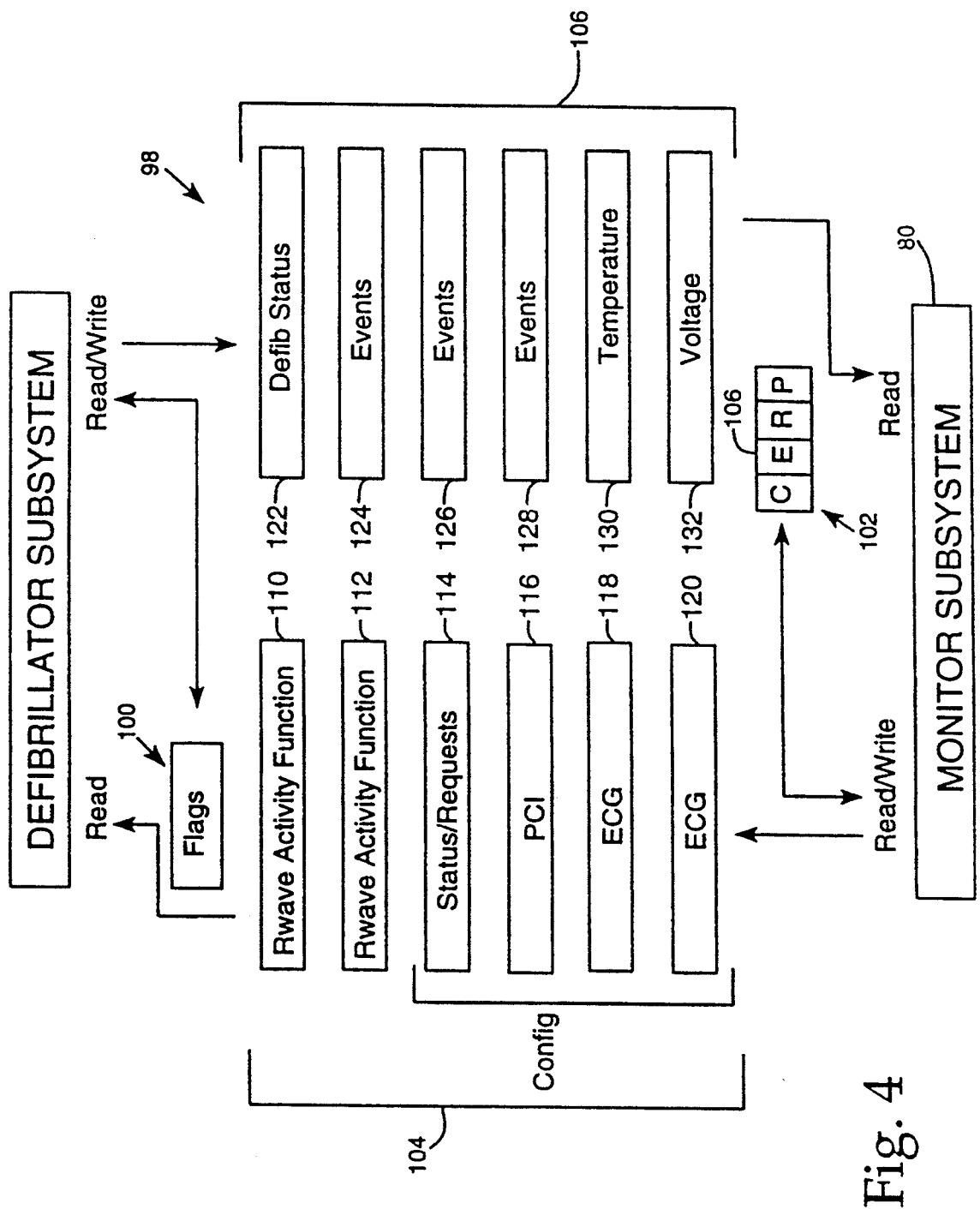
FIG. 4 is a register diagram showing organization of a mailbox interface between the defibrillator and monitor subsystems of FIG. 3.

Mailboxes 98 are provided in the defibrillator logic 72 for communication between the defibrillator subsystem and the monitor subsystem. The mailboxes are illustrated in FIG. 4. Referring to FIG. 4, the mailboxes 98 includes six registers 122, 124, 126, 128, 130 and 132 which are both readable and writable by the defibrillator subsystem. These are referred to collectively as registers 106. The monitor subsystem 80 can read but not write registers 106.

The monitor subsystem can both read and write a group of registers 104 which include registers 110, 112, 114, 116, 118 and 120. Registers 104 are readable but not writable by the defibrillator subsystem 60. Several flag registers, including flag register 100 and a interrupt register 102 are used to arbitrate access to the mailboxes, and allow some messages to be passed simultaneously. All messages and flags get cleared upon power up or shock reset. All of the registers illustrated in FIG. 4 are hardware by definition, but they are utilized by appropriate software executed in the defib logic 72 and the monitor processor 82. Accordingly, assignment of any particular hardware register for a particular type of data is arbitrary and subject to reconfiguration under software control. In the preferred embodiment, these registers have been assigned the specific meanings indicated in FIG. 4.

A flag register is used to arbitrate access to the mailbox. Four bits of register 102 are tied together to provide interrupt capability if any bit is set. The writing subsystem will set the appropriate bits in the flag register to tell the partner subsystem that data is available, and identify what kind of data it is. The reading subsystem it is. The reading subsystem will clear the flag register when it is finished reading the data.

The monitor subsystem 80 sends four types of messages to the defibrillator subsystem 60. These include configuration data, which is sent to the defibrillator subsystem during power-up using registers 114, 116, 118 and 120. Second are defibrillator requests, which are requests to the defibrillator subsystem for diagnostic information or key-control, using register 114. The third type is ECG data communicated through registers 118 and 120. Finally, the fourth is paddle contact impedance (PCI) in register 116. Once the monitor subsystem begins sending ECG data (acquired through the ECG front-end 90), it is sent at intervals, for example, every 5 milliseconds. When each set of ECG data is ready, the monitor subsystem sets the E-bit 106 in register 102 to interrupt the defibrillator subsystem. Register 102 are the four flag bits which are writable by the monitor subsystem. Flags writable by the defibrillator subsystem are those in register 100.

As noted above, the defibrillator microcontroller 62 includes a timer 63. This timer is set to a predetermined time period at least equal to the ECG data array (5 milliseconds). Preferably, it is set to approximately twice the ECG interval or 10 milliseconds to allow for timing tolerances. When the defib logic 72 receives an interrupt on the E-bit 106, it resets the timer 63. If and when timer 63 times out, i.e., it reaches the predetermined time limit, an interrupt is provided by the defibrillator microcontroller 62 to the defibrillator logic 72. The software is arranged to switch to defibrillator-only mode in response to the timer interrupt. Thus, if and when a period of at least 10 milliseconds elapses, without the E-bit interrupt being set to indicate new ECG data ready, the monitor subsystem is presumed dead. The defibrillator logic 72 switches into the defibrillator-only mode. The software reconfigures the defibrillator subsystem to allow defibrillation, but not permit synchronized cardioversion, as it would require ECG data. The system also reconfigures itself so as to enable the keypanel annunciators, i.e., audible indicators. These provide a tone for signalling defibrillator functionality to a user by actuating a charge-done signal upon completion of charging the patient's circuit to a selected energy level. The user thus is notified that the defibrillator is working and is ready for discharge, even though the CRT may be completely disabled.

The defibrillator logic 72 may continue to send information to the monitor subsystem for display on the CRT, such as energy level or charging information, even though there can be no assurance in the defib-only mode that such messages are in fact displayed to the user.

Figure 5:
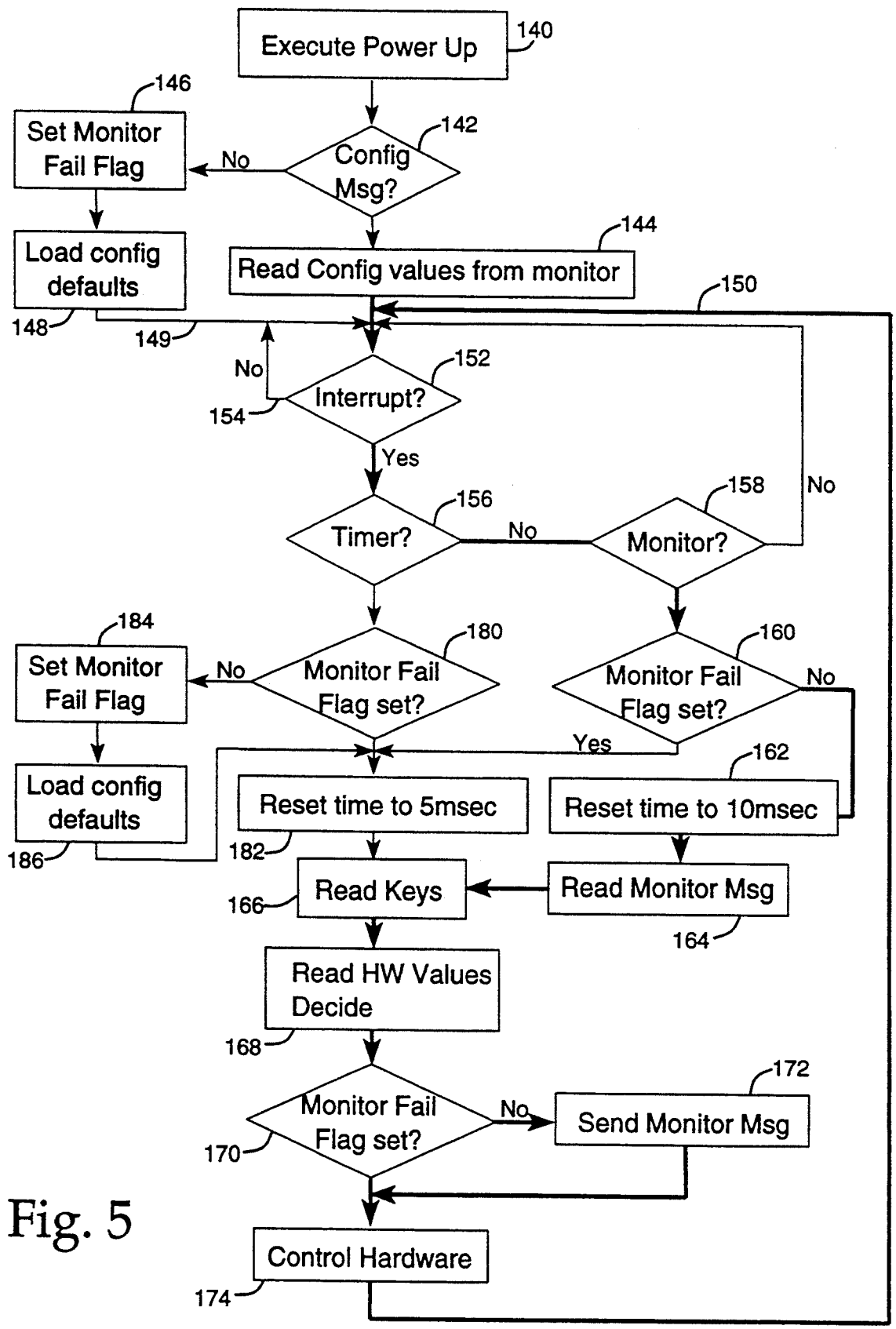
FIG. 5 is a flow diagram illustrating operation of the defibrillator control system software in pertinent part.

FIG. 5 is a flow diagram illustrating operation of the defibrillator subsystem software. Execution begins with a power up sequence 140. After power up, the software tests 142 for arrival of a configuration message from the monitor subsystem. In normal operation, a configuration message arrives and configuration values provided by the monitor subsystem are read by the defibrillator subsystem, step 144, and stored in local RAM in the defibrillator subsystem. (The monitor subsystem gets configuration data from ROM 84 and user input.) If the result of test 142 is negative, i.e., a configuration message does not arrive from the monitor subsystem as expected, it is an indication of malfunction in the monitor subsystem and, therefore, the defibrillator subsystem assumes that the monitor subsystem is dead. Accordingly, the software sets the monitor fail flag in step 146 and loads configuration defaults, step 148, which are available in the defibrillator subsystem, for defibrillator-only operation. The configuration defaults for defib-only operation include, for example, disallowing synchronized cardioversion, and enabling lights and/or tone generators for signalling a user as described above. For example, a charge-done tone maybe used to indicate to a user that the defibrillator subsystem is functional and that the patient's circuit has been charged to a selected energy level.

Next we describe the basic software loop which is executed continuously during normal operation. This loop is indicated in the flow diagram of FIG. 5 by heavy or bold lines, such as path 150. The normal operating loop description may begin with the test 152 for an interrupt. This test is simply repeated as indicated by logic path 154 until such time as an interrupt is received. In response to an interrupt, test 156 determines whether the interrupt was asserted by the timer. This refers to the timer 63 shown in FIG. 3 and described above. In normal operation, the interrupt is not asserted by the timer, and flow proceeds through to test 158 to determine whether the interrupt was asserted by the monitor subsystem. In normal operation, the interrupt is asserted by the monitor subsystem, specifically at flag 102 of FIG. 4, to indicate ECG data ready. This interrupt is asserted periodically, during normal operation, at the ECG data rate.

If it is monitor interrupt, the defibrillator subsystem software next tests 160 to determine whether the monitor fail flag is set, i.e., whether or not it was set previously. The monitor fail flag, of course, has not been set in the course of normal operation, so control proceeds to a reset step 162 in which the internal timer is reset to 10 milliseconds as discussed above. Next, the software reads monitor messages 164. These may include various messages which are passed to the defibrillator subsystem through the mailboxes as discussed above and illustrated in FIG. 4.

The next step is to read keys 166 which refer to the various push buttons and other controls on the front panel 24, also previously mentioned. Next, the software reads hardware values, step 168, and decides based on these various inputs how to control the hardware. For example, if reading the keys detected actuation of the charge buttons, the software may decide to control the patient circuit to begin charging toward an energy level selected by the user. Next, the software executes a test 170 to again determine whether or not the monitor fail flag has been set. Normally, the flag is not set, and the system proceeds to send monitor messages, step 172, which may include information for display on the front panel. Conversely, if the monitor fail flag is set, the system presumably is operating in defibrillator-only mode and sending messages to the monitor subsystem is skipped. The system proceeds in step 174 to control the hardware as previously determined, and then control flows along path 150 back to test 152 to test for a new interrupt. The foregoing steps are repeated periodically, at the ECG data rate, during normal operation.

Referring once again to the top of FIG. 5, following the power up sequence 140, the test for a configuration message 142 may fail. If no configuration message is received, the monitor subsystem is presumed dead. The software therefore sets the monitor fail flag in step 146 and proceeds to load configuration defaults in step 148. The defaults are predetermined configuration settings for configuring the subsystem for defibrillator-only operation. For example, the defaults would disallow synchronized cardioversion as a functional monitoring subsystem is a prerequisite to that function. The default configurations also would enable front panel indicator lights and tone generators for signaling a user. For example, an audible tone may be used to signal a user that the patient's circuit has charged to the selected energy level and to indicate that the defibrillator subsystem is ready for discharge. This may be the only indication to the user if the CRT display, for example, is dead. After configuration for defibrillator-only operation, the software proceeds along path 149 to the interrupt test 152.

After loading configuration defaults, control flows to the test for interrupt 152. Again, test 156 determines whether an interrupt was asserted by the internal timer. If the monitor subsystem is dead, as indicated earlier because the configuration message did not arrive. The interrupt probably is asserted by the internal timer. In that case, control flows to test 180 whether monitor fail flag is set. In this case, it was previously set (in step 146), so control flows to reset step 182 in which the internal timer is reset to a 5 millisecond interval. This is because the internal timer will now provide the periodic system timing in lieu of the ECG interrupt from the monitor subsystem. Following step 182, the software proceeds to read keys step 166 and thus enters the normal control flow described above. Execution proceeds as previously described through steps 166 and 168. Since the monitor fail flag has been set, this will be detected at test 170 and step 172 is skipped. Execution continues around loop 150 to test for the next interrupt 152. As defibrillator-only operation continues, the internal timer will provide subsequent interrupts, as detected in step 156 and it will be reset each time in step 182.

The third case is that in which power-up proceeded normally, including reading configuration values from the monitor subsystem in step 144. At some point during normal operation, however, assume the monitor subsystem fails and consequently does not assert the ECG ready interrupt. In that event, the 10 millisecond "watchdog" timer interval will be exceeded. Consequently, an interrupt detected at test 152 will be identified in step 156 as originating in the timer. Test 180 will reveal that the monitor fail flag had not been set previously, so the monitor fail flag is set in step 184, and configuration default values are loaded in step 186. Loading the configuration values is the same as step 148 described previously. Having now entered the defibrillator-only mode, the timer is reset to 5 milliseconds in step 182 and operation proceeds as described above, with the internal timer substituting for the ECG interrupt for timing purposes.

Having illustrated and described the principles of our invention in a preferred embodiment thereof, it should be readily apparent to those skilled in the art that the invention can be modified in arrangement and detail without departing from such principles. We claim all modifications coming within the spirit and scope of the accompanying claims.

We claim:

1. An integrated defibrillator/monitor system for treating a cardiac patient comprising:
   a monitor subsystem for acquiring ECG data from the patient;
   a defibrillator subsystem for delivering a shock to the patient;
   communication means disposed in the defibrillator subsystem and coupled to the monitor subsystem for communication therebetween;
   means disposed in the defibrillator subsystem and coupled to the communication means for detecting a monitor subsystem failure; and
   means in the defibrillator subsystem for switching to a defibrillator-only mode of operation in response to the monitor subsystem failure.

2. An integrated defibrillator/monitor system according to claim 1 wherein the monitor subsystem includes:
   a monitor processor means for controlling operation of the monitor subsystem;
   logic means coupled to the monitor processor means for generating data for display to an operator;
   display means coupled to the logic means for displaying the generated data;
   means for detecting failure of the logic means or the display means; and
   means coupled to the communication means for notifying the defibrillator subsystem of such failure, so that the defibrillator subsystem can switch to the defibrillator-only mode of operation.

3. An integrated defibrillator/monitor system according to claim 1 wherein the monitor subsystem includes:
   ECG data acquisition means for connection to the patient to acquire ECG data; and
   monitor processor means coupled to the ECG data acquisition means and coupled to the communication means for providing ECG data to the defibrillator subsystem; and wherein the defibrillator subsystem includes means for switching to the defibrillator-only mode when the ECG data does not arrive as expected in the communication means, whereby the defibrillator subsystem may be used while the ECG data acquisition means is not functional.

4. An integrated defibrillator/monitor system according to claim 1 wherein:
   the communication means comprises a mailbox;
   the monitor subsystem includes monitor processor means for sending periodic timing signals to the defibrillator subsystem through the mailbox;
   the defibrillator subsystem includes timing means for detecting expiration of a predetermined time limit since a periodic timing signal was last received from the monitor subsystem, thereby detecting a failure of the monitor subsystem.

5. An integrated defibrillator/monitor system according to claim 4 wherein:
   the mailbox includes a plurality of registers for communication of messages and data between the defibrillator subsystem and the monitor subsystem, one of the registers being designated as a flag register having an interrupt bit settable by the monitor subsystem for interrupting the defibrillator subsystem; and the periodic timing signals comprise periodic settings of the interrupt bit, whereby the defibrillator subsystem monitors a time elapsed since each such interrupt to detect said expiration of the predetermined time limit.

6. An integrated defibrillator/monitor system according to claim 5 wherein:
   the monitor subsystem includes ECG data acquisition means for connection to the patient to acquire ECG data;
   the monitor subsystem further includes a monitor processor coupled to the ECG data acquisition means and coupled to the mailbox for providing ECG data to the defibrillator subsystem through the mailbox at a predetermined ECG data rate;
   the interrupt bit is an ECG-ready bit, set periodically by the monitor processor to indicate ECG data ready in the mailbox; and
   the predetermined time limit is set to a value greater than the ECG data rate, whereby the defibrillator subsystem switches to the defibrillator-only mode when the ECG-ready bit is not periodically reset at the ECG data rate.

7. An integrated defibrillator/monitor system according to claim 4 wherein:
   the defibrillator system includes indicator means for informing a user that a patient circuit has charged to a selected energy level;
   the indicator means is disposed within the defibrillator subsystem; and
   the defibrillator controller includes means for actuating the indicator means to so inform a user during the defibrillator-only mode of operation.

8. A system according to claim 4 wherein the mailbox includes:
   a first register arranged to be written by the defibrillator subsystem and read by the monitor subsystem;
   a second register arranged to be written by the monitor subsystem and read by the defibrillator subsystem; and
   a flag register accessible to both subsystems for arbitrating access to the mailbox.

9. A system according to claim 4 wherein the mailbox includes a register for transmission of ECG data from the monitor subsystem to the defibrillator subsystem at predetermined regular intervals; and
   the defibrillator subsystem includes means for detecting failure of the ECG data to arrive in the said register at said regular interval.

10. A system according to claim 4 wherein:
    the detecting means includes an independent timer disposed within the defibrillator subsystem, the timer arranged to provide an interrupt upon a conclusion of a predetermined time interval starting from a reset; and the defibrillator subsystem includes a defibrillator logic arranged for resetting the independent timer responsive to each receipt of ECG data;

whereby, an interrupt from the independent timer provides an indication to the defibrillator logic of a monitor subsystem failure.

11. A system according to claim 4 wherein:

the monitor subsystem includes means for inhibiting the ECG transmission to the defibrillator subsystem to provide an indication to the defibrillator subsystem of a failure in the monitor subsystem, whereby the defibrillator subsystem switches to the defibrillator-only mode of operation.

12. In an integrated defibrillator/monitor system, a method of allowing defibrillator-only operation notwithstanding a monitor subsystem failure, the method comprising the steps of:

providing a defibrillator subsystem capable of delivering a shock to a patient;

providing a monitor subsystem, the monitor subsystem including an ECG front-end for acquiring ECG data from a patient;

transmitting a periodic clock signal from the monitor subsystem to the defib subsystem during normal operation; and in the defib subsystem, monitoring a time elapsed since each periodic clock signal arrives from the monitor and, if the elapsed time exceeds a predetermined time limit, assuming the monitor subsystem is dead, and entering the defibrillator-only mode of operation.

13. A method according to claim 12 wherein:

the monitor subsystem acquires ECG data and communicates the ECG data to the defibrillator subsystem at a predetermined ECG data rate;

the periodic clock signal is an ECG-ready signal; and the predetermined time limit is at least an inverse of the ECG data rate.

14. In an integrated defibrillator/monitor system, a method of providing a defib-only method of operation to enhance reliability, the method comprising:

partitioning the system into subsystems including a defibrillator subsystem and a monitor subsystem;

in the defibrillator subsystem, providing components sufficient to deliver a shock to a patient without communication with the monitor subsystem during a defib-only mode of operation;

in the defibrillator subsystem, monitoring operation of the monitor subsystem to detect a monitor subsystem failure; and responsive to a monitor subsystem failure, reconfiguring the defibrillator subsystem for defib-only operation.

15. A method according to claim 14 wherein the defibrillator subsystem includes a high voltage charger, a patient circuit, a paddles/pads interface, and a keypanel interface system, arranged so as to allow operation of said functions to deliver a shock to a patient without communication with the monitor subsystem during a defib-only mode of operation.

16. A method according to claim 15 further comprising:

in the monitor subsystem, providing an ECG front-end to acquire ECG data from a patient during normal operation of the system;

transmitting acquired ECG data to the defibrillator subsystem at a predetermined ECG data rate; and in the defibrillator subsystem, monitoring arrival of the ECG data so as to detect a failure of the monitor subsystem.

17. A method according to claim 16 further comprising:

in the defibrillator subsystem, deriving system timing from the ECG data rate for normal operation of the defibrillator subsystem;

providing an independent clock in the defibrillator subsystem; and in the defibrillator-only mode, employing the independent clock to provide system timing in lieu of the ECG data rate, whereby the defibrillator subsystem can function in the defib-only mode even if the ECG front-end has failed.

18. A method according to claim 16 further comprising:

in the monitor processor, detecting failure of a component of the monitor subsystem;

signaling a monitor subsystem failure to the defibrillator subsystem; and in the defibrillator subsystem, switching to the defib-only mode of operation in response to the failure signal.

19. A method according to claim 18 further comprising, in the defib-only mode of operation:

reading an energy level selected by a user;

charging the patient circuit to the selected energy level in response to a user actuating a charge button; and signalling defibrillator functionality to the user by actuating a charge done signal upon completion of charging the patient circuit.

20. A method according to claim 18 wherein switching to the defibrillator-only mode of operation includes loading a predetermined set of default configuration values, including enabling an audible charge-done signal, and disabling synchronized cardioversion.

* * * * *